United States Patent
Bassily

[19]

[11] Patent Number: 6,044,713
[45] Date of Patent: Apr. 4, 2000

[54] STRAIN MEASUREMENT SYSTEM AND METHOD

[75] Inventor: Samir F. Bassily, Los Angeles, Calif.

[73] Assignee: Hughes Electronics Corporation, El Segundo, Calif.

[21] Appl. No.: 09/307,366

[22] Filed: May 7, 1999

Related U.S. Application Data

[62] Division of application No. 08/801,446, Feb. 18, 1997, Pat. No. 5,936,165.

[51] Int. Cl.⁷ ...................................................... G01N 3/20
[52] U.S. Cl. ................................................ 73/849; 73/853
[58] Field of Search .............................. 73/849, 853, 854, 73/862.041, 862.042, 862.043, 862.044, 766, 856, 866

[56] References Cited

U.S. PATENT DOCUMENTS

| | | | |
|---|---|---|---|
| 4,636,090 | 1/1987 | Baricevac et al. ........................ | 374/56 |
| 4,811,608 | 3/1989 | Hilton ................................. | 73/862.043 |
| 4,862,751 | 9/1989 | Asakawa et al. .................. | 73/862.044 |
| 4,924,477 | 5/1990 | Gilmore et al. ........................... | 374/55 |
| 5,044,211 | 9/1991 | Whitaker .................................. | 73/866 |
| 5,121,987 | 6/1992 | Berg ...................................... | 356/357 |
| 5,123,276 | 6/1992 | Hartman et al. ...................... | 73/23.41 |
| 5,526,697 | 6/1996 | Tada et al. ......................... | 73/862.634 |
| 5,663,492 | 9/1997 | Alapati et al. ......................... | 73/64.45 |
| 5,936,165 | 8/1999 | Bassily ..................................... | 73/849 |

*Primary Examiner*—Max Noori
*Attorney, Agent, or Firm*—Georgann S. Grunebach; M. W. Sales

[57] ABSTRACT

A system for simultaneously measuring strains in a test member includes spatial-position members which are coupled to different portions of the test member and first and second displacement sensors which are spaced apart by a sensor space and coupled to the spatial-position members. Linear and bending deformations of the test member are calculated as functions of the responses of the displacement sensors and of the sensor space.

20 Claims, 5 Drawing Sheets

STRAIN MEASUREMENT SYSTEM AND METHOD

This application is a division of Ser. No. 08/801,446, filed Feb. 18, 1997, now U.S. Pat. No. 5,936,165.

BACKGROUND OF THE INVENTION

1. Field of the Invention

The present invention relates generally to measurement systems and more particularly to strain measurement systems.

2. Description of the Related Art

Coefficient of thermal expansion (CTE) is the fractional increase in size of a member per unit rise in temperature. If the member increases in length from an initial length $L_i$ to a final length $L_f$ when its temperature is raised by $\theta$ units of temperature, the coefficient of thermal expansion $\alpha$ is related to these parameters by the expression of $L_f = L_i(1 + \alpha\theta)$. This expression can be rearranged to define $\alpha$ as $$\alpha = \left(\frac{1}{\theta}\right)\frac{\Delta L}{L_i} = \frac{\varepsilon}{\theta} \qquad (1)$$

in which $\Delta L$ is a differential length given by $L_f - L_i$ and $\varepsilon$ is the thermal strain $\Delta L/L_i$ which is induced in the member by the temperature rise. As shown by equation (1), the measurement of CTE involves the measurement of strain and differential temperature. Thus, any system which measures strain can be adapted for the more specific measurement of CTE.

Conventional techniques for measuring CTE include dilatometry and interferometry. In dilatometry, the expansion of a test member is compared to the expansion of a reference member whose CTE is either known or is negligible relative to the CTE of the test member. Rather than measuring the initial and final lengths ($L_i$ and $L_f$) of the test member, dilatometry measures the difference in length $\delta L$ between the test member and the reference member. Because $\delta L$ is generally much less than $L_i$ and $L_f$, the measurement accuracy is enhanced. Error sources in dilatometry include an imperfect knowledge of the reference member's CTE and inadvertent temperature differences between the test member and the reference member.

In interferometry, the expansion of a test member is measured relative to the wavelength of monochromatic light. A monochromatic light beam is split into first and second signals which are directed along first and second optical paths before being recombined. The optical paths are configured to include reflection from opposite ends of the test member. The difference in the optical path lengths causes a phase difference in the first and second signals which affects the amplitude of the recombined signal.

Expansion of the test member causes the first and second optical path lengths to change and this change is reflected in a change in the amplitude of the recombined signal. The measurement accuracy can be on the order of the radiation wavelength which is generally small, e.g., ~1 micron for visible light. Interferometry measurement systems are typically complex and expensive. Error sources include the temperature sensitivities of optical equipment (e.g., lenses and retroreflectors) which must be exposed to the test temperature.

Dilatometry and interferometry measurement techniques are best suited for the measurement of homogeneous test members which expand linearly. Because their constituent parts may have different CTEs, composite members often bend or twist as they expand. Conventional dilatometry and interferometry techniques are typically not configured to correct for this complex expansion.

Figures 1, 2:
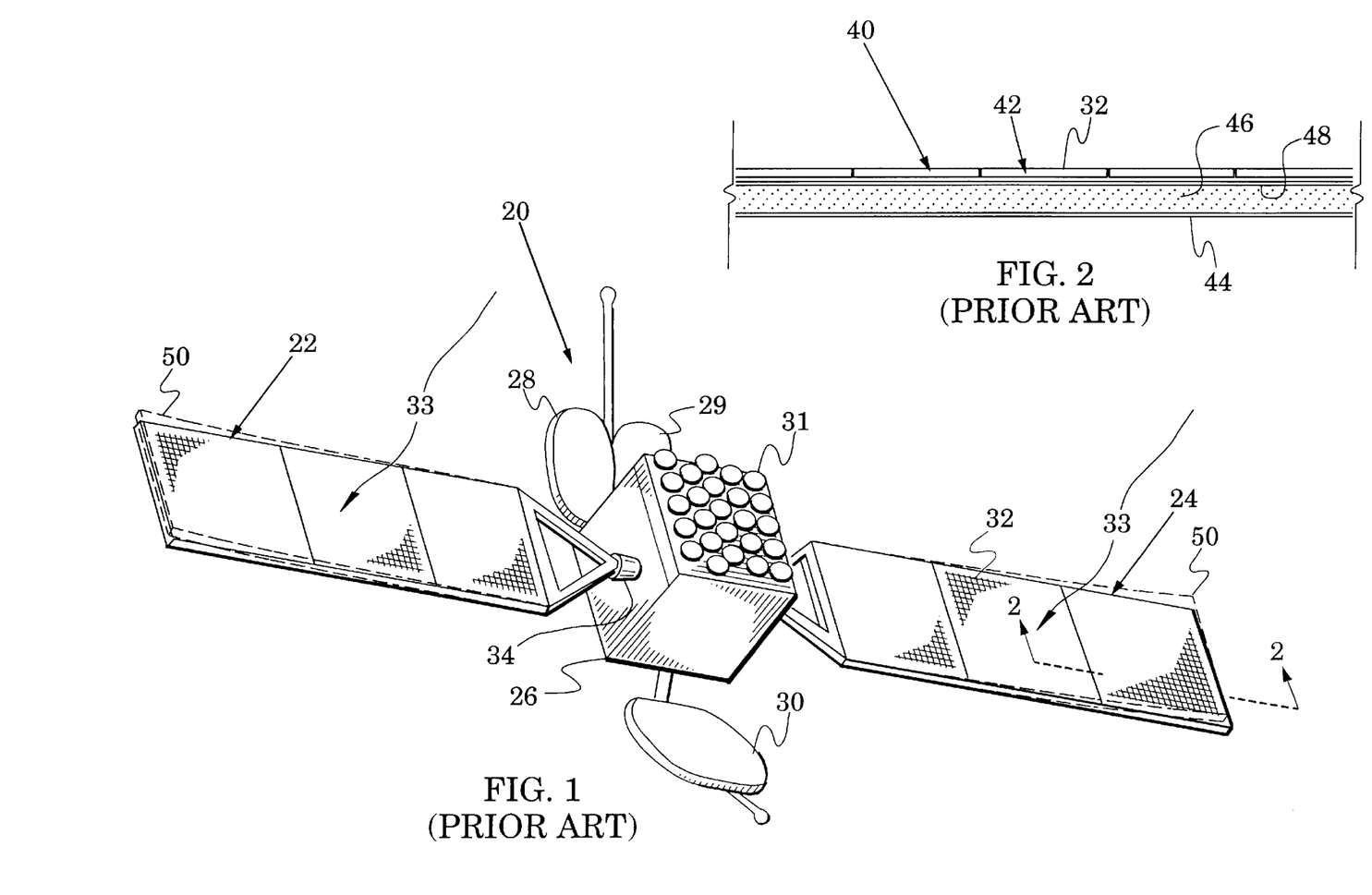
FIG. 1 is a perspective view which illustrates bending of a pair of solar wings in a satellite in which the bending is caused by solar heating.
FIG. 2 is a view along the plane 2—2 of FIG. 1.

Exemplary composite members which are subjected to thermal stress are the solar wings 22 and 24 of the satellite 20 of FIG. 1. The satellite has a body 26 which carries various communication antennas, e.g., dish antennas 28, 29 and 30 and an array antenna 31. The solar wings 22 and 24 extend in opposite directions from the body 26 and they each carry a plurality of solar cells 32 on one wing face.

The satellite 20 is typically maintained in an attitude which directs the antennas at the Earth. The solar cells 32 convert solar radiation 33 to electrical energy for operation of the systems of the spacecraft 20. Accordingly, the solar wings 22 and 24 are connected to the body 26 with gimbals 34 so that they can be rotated towards the sun in order to enhance the reception of the solar radiation 33.

The cross section of FIG. 2 shows that each solar wing is typically formed as a composite panel 40 which has dissimilar skins 42 and 44 on opposite sides of a core 46. In an exemplary panel 40, the core 46 is aluminum honeycomb and the lower skin 44 is formed of a sheet of graphite epoxy composite. The upper skin 42 includes another sheet 48 of a graphite epoxy composite which adjoins the core 46 and the solar cells 30 which are bonded to the sheet 48. The solar cells 30 are typically carried on silicon substrates and covered with clear glass covers and are arranged in an adjoining relationship. The solar cells 30 have an exemplary thickness of 0.5 millimeters and the panel 40 has an exemplary thickness of 40 millimeters.

Thus, the composite panel 40 is substantially an aluminum honeycomb core with one skin of graphite epoxy and an opposite skin of graphite epoxy paved with higher-expansion solar cells. As its orbits about the Earth take the satellite 20 into and out of the Earth's shadow, the solar wings 22 and 24 are subjected to cycles of heating by the solar radiation 33. Because the spaced skins 42 and 44 have different CTEs, the solar wings bend from a first spatial shape which is indicated by solid lines in FIG. 1 to a second spatial shape which is indicated by broken lines 50. This bending induces torques upon the satellite 20 which disturb its attitude. As the satellite 20 moves into and out of the Earth's shade, the bending occurs so suddenly that it has commonly been referred to as "solar snap". In low earth orbits, the induced torques of some solar panels can be sufficient to overwhelm the attitude control systems of the satellite.

Accordingly, it is important to measure the linear and bending deformations of the composite panel 20 to evaluate the torques that will be induced upon a satellite. Accurate knowledge of these deformations can be used to design panels with decreased deformation and/or to accurately predict the torques that will be required of the satellite's attitude control system.

SUMMARY OF THE INVENTION

The present invention is directed to measurement systems which can simultaneously measure linear and bending deformations of composite test members. This goal is achieved with a measurement system in which:

a) first and second spatial-position members are coupled to respective portions of a test member so as to be responsive to spatial movements of those portions, and b) first and second displacement sensors are separated by a sensing space and respectively coupled to the first and second spatial-position members.

In one measurement system embodiment, the spatial-position members are quartz rods which are positioned in a common vertical plane and which lie in the bottom of passages through the test member. The first and second displacement sensors each have upper and lower pendulums that are coupled to displacement elements of a displacement transducer. Each pendulum is suspended from a respective quartz rod and coupled to a respective displacement element so that the displacement elements freely move relative to each other.

The novel features of the invention are set forth with particularity in the appended claims. The invention will be best understood from the following description when read in conjunction with the accompanying drawings.

DETAILED DESCRIPTION OF THE PREFERRED EMBODIMENTS

Figure 3:
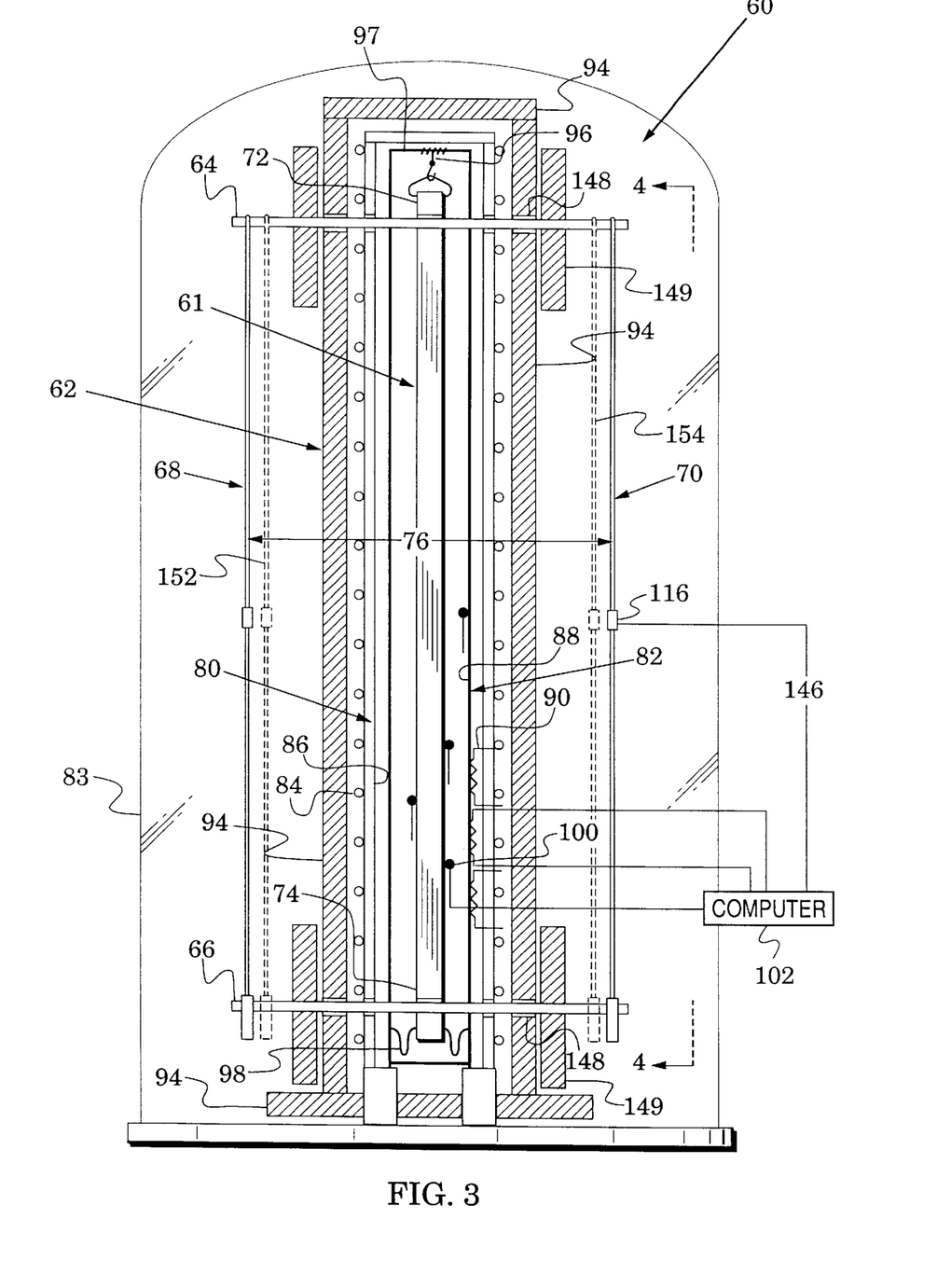
FIG. 3 is a partially-sectioned elevation view of a measurement system for the measurement of coefficient of thermal expansion (CTE)

FIG. 3 illustrates a measurement system 60 for measuring linear and bending deformations in a test member 61 (e.g., a test article or test sample). The measurement system 60 includes a thermal chamber 62 which is configured to receive the test member 61 and subject it to a range of temperatures.

The system 60 also includes spatial-position members 64 and 66 and displacement sensors 68 and 70. The spatial-position members 64 and 66 are coupled to upper and lower portions 72 and 74 of the test member 61. The displacement sensors 68 and 70 are spaced apart by a sensor space 76 and are each coupled between the spatial-position members 64 and 66.

The measurement system 60 facilitates the measurement of linear and bending deformations in the test member 61 because these deformations are determinable functions of the responses of the first and second displacement sensors 68 and 70 and of the sensor space 76. Further description of the spatial-position members 64 and 66 and displacement sensors 68 and 70 is preceded by the following detailed description of the thermal chamber 62.

The thermal chamber 62 includes a cooling system 80 and a heating system 82, both of which are positioned within a vacuum enclosure in the form of a bell jar 83. The cooling system 80 has a plurality of cooling coils 84 which are arranged in a conventional serpentine relationship to carry a coolant, e.g., liquid nitrogen, and also arranged to define a cooling chamber 86. The heating system 82 has a heating chamber 88 which is positioned within the cooling chamber 86. The heating chamber 88 is formed by a box of a metal, e.g., aluminum, whose outer surface is covered with conventional heating elements 90 (exemplary heating elements are schematically indicated by resistors adjoining the chamber 88). Exemplary film heating elements are carried on a polyimide film manufactured under the trademark Kapton by E.I. du Pont de Nemours & Company.

The cooling system 80 is enclosed by an insulation envelope 94. Because the vacuum of the bell jar 83 effectively reduces thermal convection from the cooling chamber 86 and heating chamber 88, the insulation envelope 94 is primarily configured to reduce thermal radiation. An exemplary insulation envelope 94 is formed of several layers of metallized polyamide polymer film and each additional layer adds a further reduction of radiation. Such layered radiation-blocking blankets are commonly used in satellites and are conventionally known as Multi Layer Insulation (MLI) blankets.

The test member 61 is positioned within the heating chamber 88 and vertically suspended within the thermal chamber 62, e.g., by wires 96 from two suspension rods 97 which are supported at the top of the heating chamber 88. To stabilize the test member 61 and prevent pendulum-like oscillations, resilient members 98 (e.g., folded rubber tabs) are placed between lower corners of the test member 61 and the heating chamber 88. A plurality of thermocouples 100 (for clarity of illustration, only a few exemplary thermocouples are shown) are spaced over the test member 61 and the heating chamber 88. The thermocouples 100 and heating elements 90 are connected to a computer 102 to form a portion of a thermal control system (the heating element current sources are not shown).

In an exemplary operation of the thermal chamber 62, the air pressure within the bell jar 83 is reduced to a near vacuum, e.g., to $<1 \times 10^{-4}$ Torr. Coolant is sent through the cooling coils 84 until they are stabilized at a low temperature near the boiling point of the cooling liquid, e.g., −185° Centigrade. The heating elements 90 are then controlled by the computer 102 to cycle the test member 61 and the heating chamber over a desired test range of temperatures as sensed by the thermocouples 100. Preferably, the cooling chamber is maintained at a constant temperature throughout the measurement cycles so that temperature control is effected only by the current through the heating elements 90.

FIGS. 4–7 illustrate details of the spatial-position members 64 and 66 and displacement sensors 68 and 70. For clarity of illustration, the displacement sensors 68 and 70 are not shown in FIGS. 5 and 6A. These latter figures show passages 110 which are prepared (e.g., by drilling) in the upper and lower portions 72 and 74 of the test member 61. Care is taken to insure that the passages 110 are horizontal and parallel and lie in a common vertical plane. Care is also taken to insure that the spatial-position members 64 and 66 are substantially supported only near the extreme ends of the passages (e.g., on the face sheets of an exemplary honeycomb sandwich panel).

Figures 4, 5, 6A, 6B, 7:
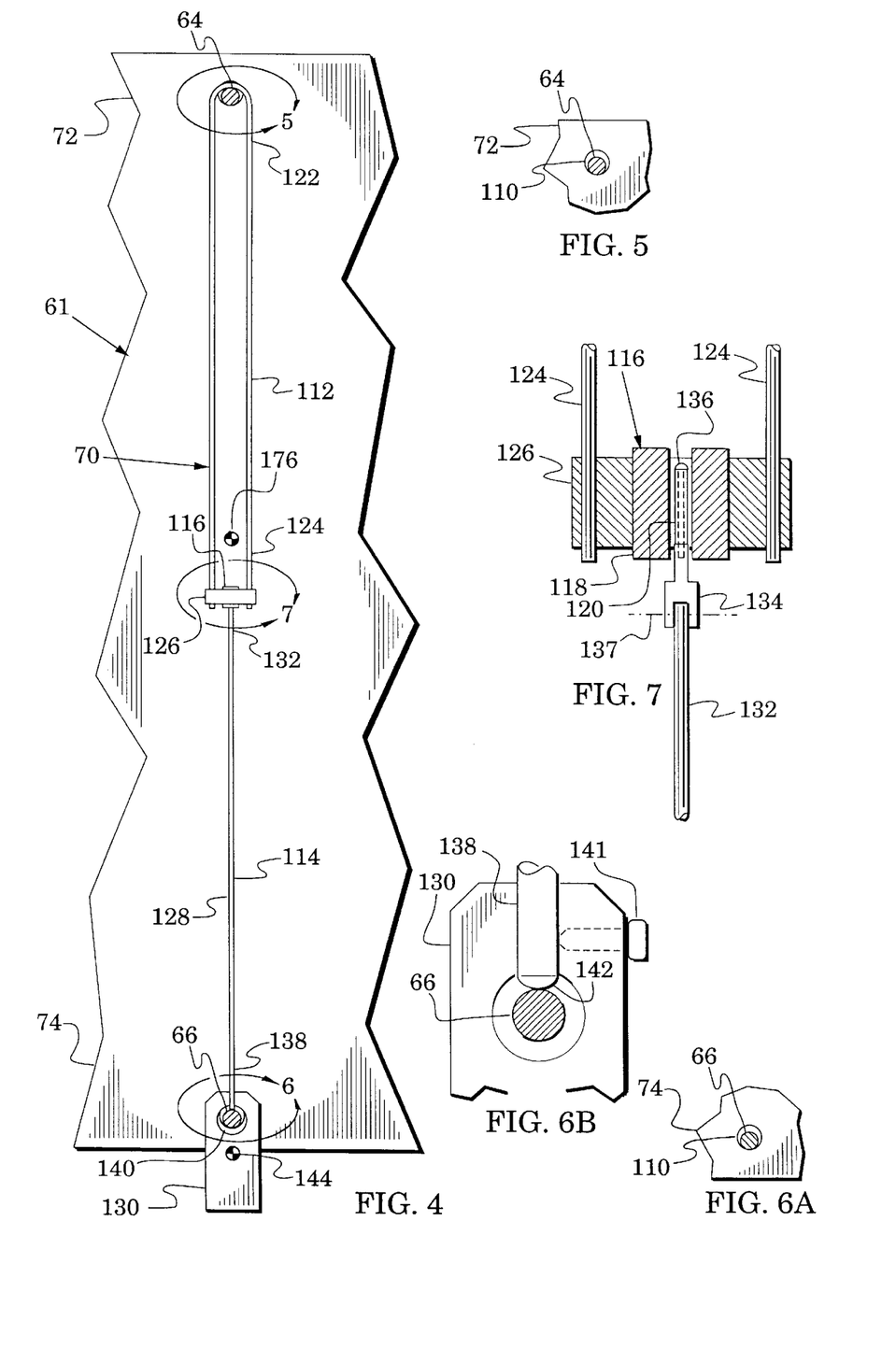
FIG. 4 is an enlarged view along the plane 4—4 of FIG. 3.
FIG. 5 is a view of structure within the curved line 5 of FIG. 4 with a displacement sensor removed.
FIG. 6A is a view of structure within the curved line 6 of FIG. 4 with a displacement sensor removed.
FIG. 6B is an enlarged view of structure within the curved line 6 of FIG. 4.
FIG. 7 is a sectional, enlarged view of structure within the curved line 7 of FIG. 4.

The spatial-position members 64 and 66 are preferably rods of a material with a low CTE, e.g., quartz. The spatial-position members 64 and 66 preferably have a diameter that is less than that of the passages 110 so that the members contact the bottom of the passages 110 when the members are received into the passages. To insure that the spatial-position members 64 and 66 do not move axially in the passages 110, resilient members such as O-rings can be placed over the spatial-position members 64 and 66 and abutted with the test member 61.

The displacement sensor 70 (the displacement sensors 68 and 70 are identical) includes an upper pendulum 112, a lower pendulum 114 and a displacement transducer 116 which is coupled between the upper and lower pendulums. Although a variety of displacement transducers can be used in the invention, miniature linear voltage displacement transducers (LVDT) are especially suitable for use in the measurement system 20 (an exemplary LVDT is a Schaevitz model #025 manufactured by Lucas Schaevitz of Pennsauken, N.J.). The displacement transducer 116 has first and second displacement elements which, in an exemplary LVDT, are an electric coil 118 and a magnetic core 120 which is slidingly received within the coil 118.

The upper pendulum 112 is a quartz U-shaped rod whose upper end 122 is suspended from the spatial-position member 64 and whose lower end 124 is coupled to the coil 118 (e.g., by a mounting block 126 and set screws which are not shown). The lower pendulum 114 includes a quartz rod 128 and a counterweight 130. The upper end 132 of the rod 128 is coupled to the core 120 (e.g., by a cup 134 and a screw 136 with the cup attached to the upper end 132 (e.g., with a set screw) as indicated by an attachment centerline 137). The lower end 138 of the rod 128 abuts the spatial-position member 66.

As specifically shown in FIG. 6B, the counterweight 130 is attached to the lower rod end 138 but has an oversized hole 140 which is arranged so that the counterweight 130 does not abut the spatial-position member 66. Instead, the rod end 138 is secured in the counterweight 130 by a set screw 141 and the rod end 138 terminates in a beveled or rounded terminus 142 which abuts the spatial-position member 66. The mass of the counterweight 130 is sufficient to position the center of gravity 144 of the lower pendulum 114 below the spatial-position member 66. Thus, the lower pendulum 114 hangs from and can swing about the spatial-position member 66, with the rod lower end 138 abutting the spatial-position member 66.

The upper and lower pendulums 112 and 114 are vertically aligned so that the core 120 freely slides within the coil 118 of the displacement transducer 116. The coil 118 is coupled to the computer 102 (as indicated schematically by line 146 in FIG. 3) so that the coil's current and voltage, and hence the displacement between the spatial-position members 64 and 66, can be monitored. The heating chamber 88, the cooling chamber 86 and the insulation envelope 94 are arranged so that they are spaced from the spatial-position members 64 and 66, e.g., by the holes 148 in the insulation envelope 94 in FIG. 3. Radiation through the holes 148 is reduced by supplementary insulation members 149 that are carried over the spatial-position members 64 and 66.

To provide backup or to confirm the data from the displacement sensors 68 and 70, an additional set of displacement sensors 152 and 154 (shown in broken lines in FIG. 3) can be added to the measurement system 60.

In operation of the measurement system 60, the test member 61 is prepared and positioned within the thermal chamber 62. The temperature of the thermal chamber is then cycled by the thermal control system and the computer 102 receives and stores temperatures from the thermocouples 100 and corresponding displacement data from the displacement transducers of the displacement sensors 68 and 70.

With knowledge of the sensor space (76 in FIG. 3) and the displacement data from the displacement sensors 68 and 70, linear and bending deformations of the test member 61 can be obtained. This process can be described with reference to the schematic representation 160 of FIG. 8. This figure shows the displacement sensors 68 and 70 spaced by a sensor space S (same as the sensor space 76 of FIG. 3) and coupled between the spatial-position members 64 and 66. The spacings between the test member's centerline 162 and the displacement sensors 68 and 70 are respectively referenced as $S_f$ and $S_b$ (the subscripts f and b refer to front and back relative to the test member 61).

Figure 8:
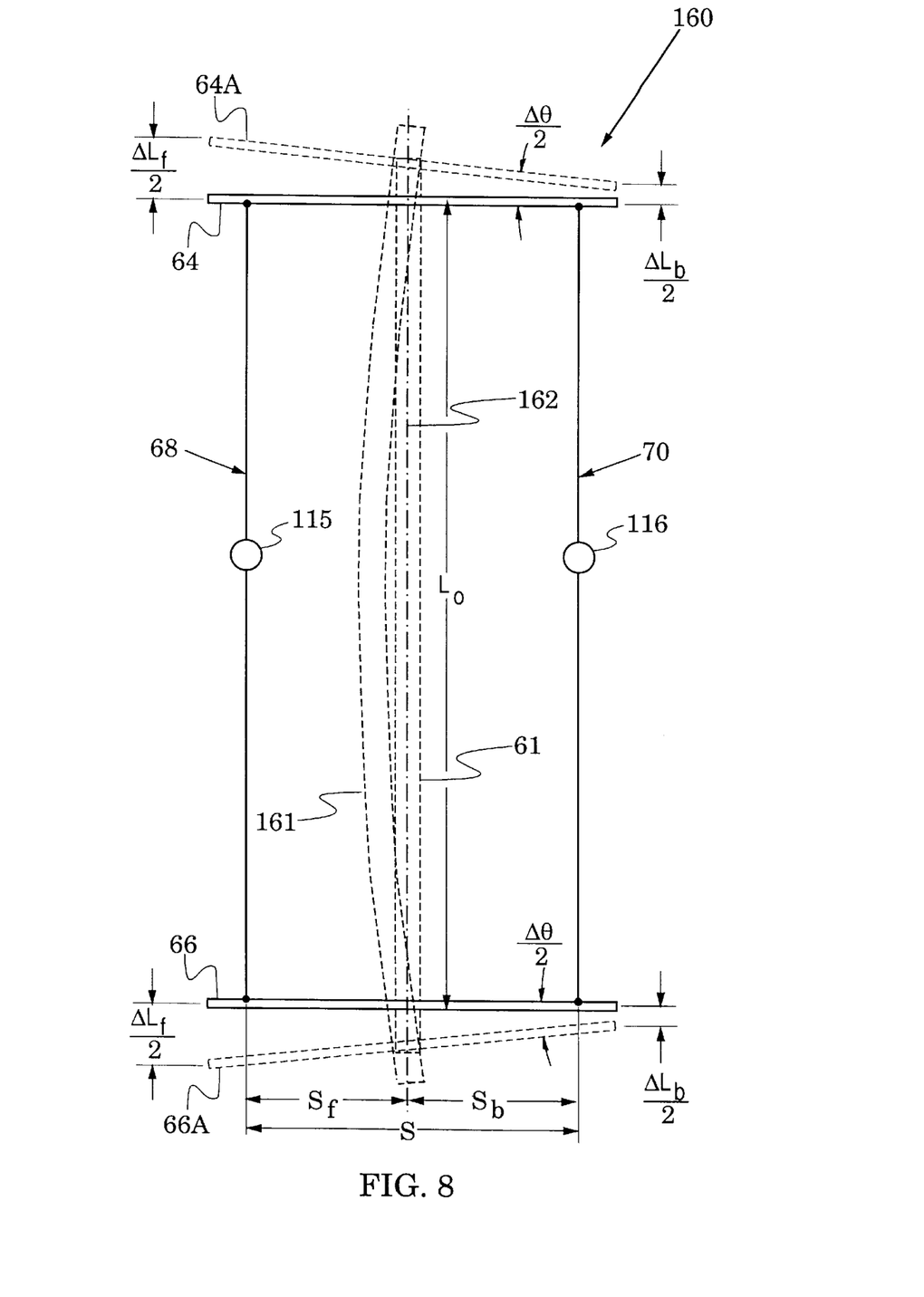
FIG. 8 is a schematic of the measurement system of FIG. 3.

If the test member is a composite (e.g., the panel 40 of FIG. 2), it will generally exhibit both linear and bending deformations as it is subjected to temperature variations. Accordingly, the test member 61 is shown in FIG. 8 to have an initial configuration 61 and a final, deformed configuration 161.

Because they lie in the bottom of the test member passages (110 in FIGS. 5 and 6), the spatial-position members 64 and 66 move away from each other and rotate as the test member 61 expands and bends to its final configuration 161. This test member deformation causes the spatial-position members 64 and 66 to rotate relative to each other to final positions 64A and 66A (for clarity of illustration, the deformation of the test member 61 is greatly exaggerated in FIG. 8 and is shown to be symmetric about its mid-point). As a result of the deformation, a displacement transducer 115 of the displacement sensor 68 senses a differential length $\Delta L_f$ and a displacement transducer 116 of the displacement sensor 70 senses a differential length $\Delta L_b$.

Prior to a test, the test member 61 has an initial length $L_O$ between the spatial-position members 64 and 66. The test member may also have an initial curvature $\theta_O$ (not specifically shown in FIG. 8) in which curvature $\theta$ is the angle between an upper normal to the test member 61 at the spatial-position member 64 and a lower normal to the test member 61 at the spatial-position member 66. After deformation of the test member to the deformed position 161, the curvature is $\theta_O + \Delta\theta$ in which $\Delta\theta$ indicates the bending deformation due to the temperature difference.

The linear and bending deformations of the test member 61 are functions of the responses of the displacement sensors 68 and 70 and of the sensor space S. Accordingly, various linear and bending deformations can be calculated with the data received by the computer (102 in FIG. 3).

For example, the bending deformation $\Delta\theta$ between the test member's initial configuration 61 and its final configuration 161 is given by $$\Delta\theta = 2\sin^{-1}\left[\frac{(\Delta L_f - \Delta L_b)}{2S}\right]. \tag{2}$$

Also, it can be shown that the centerline strain $\epsilon_{cl}$ along the test member's centerline 162 is given by $$\epsilon_{cl} = \left(1 + \frac{\Delta L_f S_b + \Delta L_b S_f}{SL_o}\right)\left(\frac{\theta_o + \Delta\theta}{\sin\left(\frac{\theta_o + \Delta\theta}{2}\right)}\right)\left(\frac{\sin\frac{\theta_o}{2}}{\theta_o}\right) - 1 \tag{3}$$

and the strain at any plane of the test member 61 which is spaced a distance D from the centerline 162 is given by $$\varepsilon_S = \left(1 + \frac{\Delta L_f(S_b + D) + \Delta L_b(S_f - D)}{SL_o}\right)\left(\frac{\theta_o + \Delta\theta}{\sin\left(\frac{\theta_o + \Delta\theta}{2}\right)}\right)\left(\frac{\sin\frac{\theta_o}{2}}{\theta_o}\right) - 1. \quad (4)$$

In most practical applications of the invention, $\theta_O$ is sufficiently small (e.g., <10 milliradians) so that equation (2) can be written as $$\Delta\theta = \frac{(\Delta L_f - \Delta L_b)}{2S}.$$

Under somewhat more restrictive conditions (e.g., when both $\theta_O$ and $\Delta\theta$ are <3 milliradians), equations (3) and (4) can be approximated as $$\varepsilon_{cl} = \frac{\Delta L_f S_b + \Delta L_b S_f}{SL_o}$$

and $$\varepsilon_S = \frac{\Delta L_f(S_b + D) + \Delta L_b(S_f - D)}{SL_o}.$$

Figure 9:
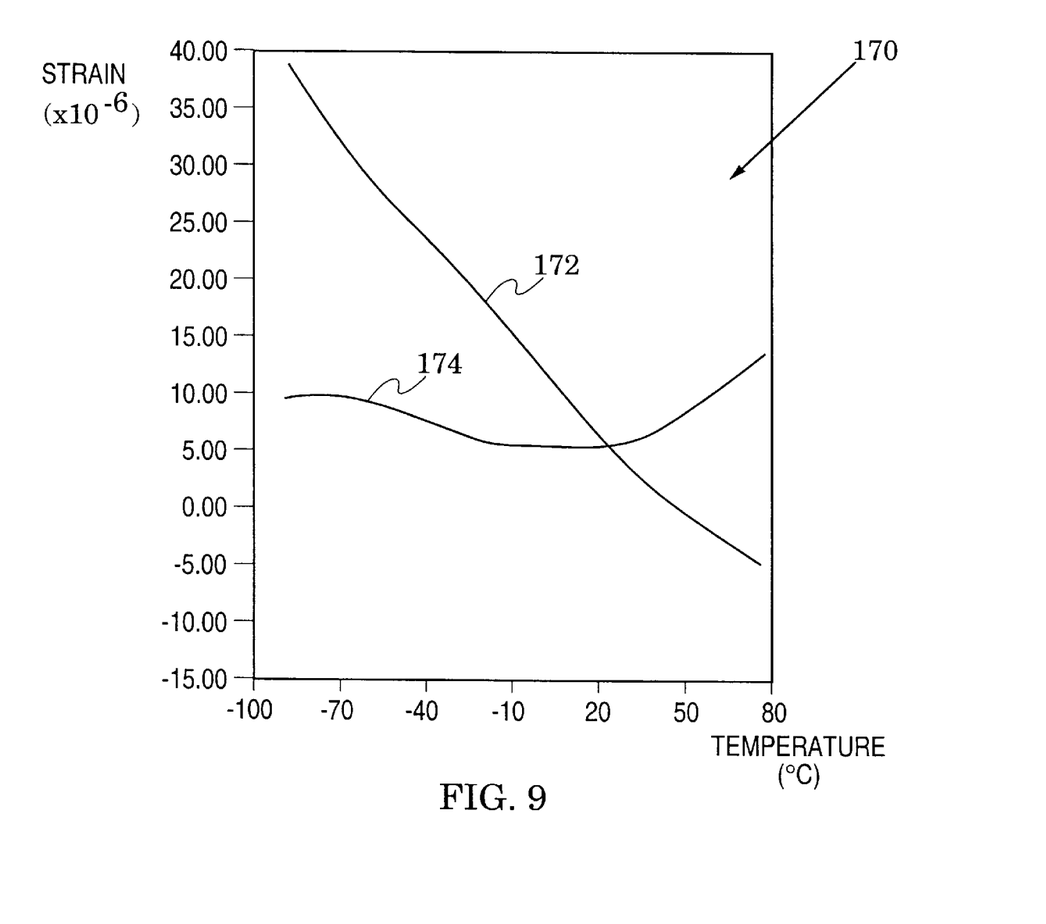
FIG. 9 is a graph showing strains measured with the system of FIG. 3 in a composite panel similar to the panel of FIG. 2.

An exemplary panel was formed to simulate the panel 40 of FIG. 2. In this panel the solar cells 32 were replaced with glass blanks. This panel was placed in the measurement system of FIG. 3 and temperature data was recorded with the computer 102. This data was then reduced with equation (4) to find the strain in the opposite skins 42 and 44 of the panel 40 of FIG. 2. The calculated strains are plotted in the graph 170 of FIG. 9, which shows a plot 172 of the strain in the sheet 44 and a plot 174 of the strain in the sheet 42. These strains can be used to find the CTE across any temperature range with the use of equation (1) above. Plot 174 particularly shows that CTE is, in general, a function of temperature.

The system and methods of the invention permit measurement of linear and bending deformations in test members. The system is simple, inexpensive and accurate and does not require a reference member or an extensive optical arrangement.

The teachings of the invention facilitate a number of strain measurement advantages. As specifically shown in FIGS. 4–7, the invention teaches displacement sensors 68 and 70 which each have upper and lower pendulums 112 and 114 that hang respectively from spatial-position members 64 and 66. The upper and lower pendulums are respectively coupled to an electric coil 118 and a magnetic core 120 of a displacement transducer.

The novel pendulum structure facilitates free, nonbinding movement between the transducer elements. Such movement is enhanced by causing the dimensions and weights of the upper and lower pendulums (112 and 114 in FIG. 4) to be in the same proportion so that lateral contact forces between the body and core (118 and 120 in FIG. 7) of the displacement transducers 115 and 116 result in equal angular rotations of the upper and lower pendulums. This maintains the alignment of the core with the body as the upper and lower spatial position members 64 and 66 move slightly relative to each other.

It can be shown that this condition is satisfied when the ratio of the distances between a displacement transducer and the upper and lower spatial position members (i.e., the lengths of the upper and lower pendulums) equals the ratio of the moments of inertia of the upper and lower pendulums.

In particular, the moment of inertia of the upper pendulum 112 is the product of its mass and the distance between its center of gravity (176 in FIG. 4) and its effective pivot point at the center of the spatial position member 64. Similarly, the moment of inertia of the lower pendulum 114 is the product of its mass and the distance between its center of gravity (144 in FIG. 4) and its effective pivot point which is the terminus 142 of FIG. 6B. The moment of inertia in the above description is typically more completely referred to as the first moment of inertia.

The structure of the displacement sensors 68 and 70 and the upper spatial-position members 64 and 66 also facilitates positioning the displacement transducers on the outer side of an insulation envelope (94 in FIG. 3). Thus, the displacement transducers are not exposed to substantial temperature variations which would otherwise affect the strain measurement of the test member because of transducer temperature sensitivity.

The arrangement of the spatial-position members 64 and 66 and the displacement sensors 68 and 70 also facilitates structural scaling to accommodate different sized test members. For example, strain measurement accuracy is enhanced in a test of spacecraft solar wing structures by using a test sample whose size is sufficient to include a large number of solar cells. The structural arrangement of the invention permits the measurement system 60 of FIG. 3 to be easily scaled up to receive such a large test sample.

Strain measurement accuracy is further enhanced by structures of the invention which facilitate near-uniform temperatures across test members. Preferably, the walls of the cooling and heating chambers (86 and 88 in FIG. 3) are made of highly conductive metals (e.g., aluminum and copper) and thermal coupling is enhanced by continuously bonding the heating elements 90 to the walls with thin conductive film adhesives and continuously brazing the cooling coils 84 to the chamber walls.

The outer cooling chamber 86 is preferably kept at a near-uniform temperature by flooding the cooling coils 84 with liquid nitrogen which places the outer chamber in a phase-change (boiling) heat-transfer regime that maintains a constant temperature despite heat flux variations that are received from the inner heating chamber 88. Additional heat flux variations change the phase (liquid to gaseous) of the coolant without changing its temperature, i.e., the coolant temperature remains at the liquid nitrogen's boiling temperature as long as some liquid remains in each of the coils 84. This phase-change, heat-transfer regime can be realized, for example, by monitoring the nitrogen temperature at a coolant exit and adjusting the nitrogen flow rate to maintain the exit temperature in a predetermined range, e.g., −185 to −190 degrees centigrade.

Not only does this technique result in a very uniform temperature over the surface of the test member, but it simplifies controlling the temperature because both hot and cold test member temperatures can be achieved by simply varying the level of electric power supplied to the heating chamber. Simulataneously, the coolant supply is thermostatically maintained near its boiling temperature. An added advantage of maintaining the cooling chamber temperature constant during a test is that the temperature of the outer surface of the MLI blanket (94 in FIG. 3), and subsequently the temperature of the displacement transducers (115 and 116 in FIG. 3), remains constant throughout the test. Thus, errors caused by transducer temperature sensitivity are eliminated.

Although the invention has been described with reference to the measurement of temperature-induced strains, the teachings of the invention can obviously be applied to measurement of strains which are induced by any other effect (e.g., moisture desorption).

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

I claim:

1. A measurement system for simultaneously measuring linear and bending deformations in a test member, comprising:

a first spatial-position member adapted to be coupled to a first portion of a test member so as to be responsive to spatial movements of said first portion;

a second spatial-position member adapted to be coupled to a second portion of said test member so as to be responsive to spatial movements of said second portion; and first and second displacement sensors each coupled between different respective locations on said first and second spatial-position members, with said first and second displacement sensors spaced apart by a sensor space and producing responses corresponding to changes in the distances between their respective locations on said first and second spatial-position members;

the responses of said first and second displacement sensors being a function of said linear and bending deformations and said sensor space.

2. The measurement system of claim 1, wherein said first and second displacement sensors each include a displacement transducer coupled between said first and second spatial-position members.

3. The measurement system of claim 1, wherein:

said first and second spatial-position members are positioned in a substantially vertical plane with said first spatial-position member above said second spatial-position member; and each of said first and second displacement sensors includes;
a) a displacement transducer having first and second displacement elements and which is responsive to displacement between said first and second displacement elements;
b) an upper pendulum having a first end which is suspended from said first spatial-position member and a second end which is coupled to said first displacement element; and
c) a lower pendulum having a first end which is coupled to said second displacement element and a second end which is suspended from said second spatial-position member.

4. The measurement system of claim 3, wherein the upper pendulum of each displacement sensor is formed of quartz.

5. The measurement system of claim 3, wherein said first and second spatial-position members are formed of quartz.

6. The measurement system of claim 3, wherein the lower pendulum of each displacement sensor includes:

a rod having an upper and a lower end which respectively form said first and second ends of said lower pendulum; and a counterbalance coupled to said rod lower end to maintain said rod in a vertical position.

7. A measurement system for measuring linear and bending deformations in a test member due to temperature change, comprising:

a thermal chamber configured to receive a test member and to generate a range of temperatures;

a first spatial-position member adapted to be coupled to a first portion of said test member so as to be responsive to spatial movements of said first portion;

a second spatial-position member adapted to be coupled to a second portion of said test member so as to be responsive to spatial movements of said second portion; and first and second displacement sensors each coupled between different respective locations on said first and second spatial-position members, with said first and second displacement sensors spaced apart by a sensor space and producing responses corresponding to changes in the distances between their respective locations on said first and second spatial-position members;

the responses of said first and second displacement sensors being a function of said linear and bending deformations and said sensor space.

8. The measurement system of claim 7, wherein said thermal chamber includes:

a cooling chamber with an associated cooling system for said cooling chamber; and a heating chamber with an associated heating system for said heating chamber, said heating chamber positioned within said cooling chamber.

9. The measurement system of claim 8, wherein said cooling system includes cooling coils arranged about said cooling chamber and configured to receive liquid nitrogen.

10. The measurement system of claim 8, wherein said heating system includes film heating elements arranged about said heating chamber.

11. The measurement system of claim 8, wherein said thermal chamber includes:

a vacuum enclosure; and a thermal insulating envelope positioned within said vacuum enclosure and arranged to substantially surround said cooling chamber.

12. The measurement system of claim 7, wherein said first and second displacement sensors each include a displacement transducer.

13. The measurement system of claim 7, wherein:

said first and second spatial-position members are positioned in a substantially vertical plane with said first spatial-position member above said second spatial-position member; and each of said first and second displacement sensors includes;
a) a displacement transducer having first and second displacement elements and which is responsive to displacement between said first and second displacement elements;
b) an upper pendulum having a first end which is suspended from said first spatial-position member and a second end which is coupled to said first displacement element; and
c) a lower pendulum having a first end which is coupled to said second displacement element and a second end which is suspended from said second spatial-position member.

14. The measurement system of claim 13, wherein the upper pendulum of each displacement sensor is formed of quartz.

15. The measurement system of claim 13, wherein said first and second spatial-position members are formed of quartz.

16. The measurement system of claim 13, wherein the lower pendulum of each displacement sensor includes:

a rod having an upper and a lower end which respectively form said first and second ends of said lower pendulum; and a counterbalance coupled to said rod lower end to maintain said rod in a vertical position.

17. A method for measuring linear and bending deformations in a test member, comprising the steps of:

coupling a first spatial-position member to a first portion of a test member so as to be responsive to spatial movements of said first portion;

coupling a second spatial-position member to a second portion of said test member so as to be responsive to spatial movements of said second portion;

sensing a first displacement between said first and second spatial-position members along a first plane;

sensing a second displacement between said first and second spatial-position members along a second plane that is spaced from said first plane by a sensing space; and obtaining an indication of said linear and bending deformations as a function of said first and second displacements and of the magnitude of said sensing space.

18. The method of claim 17, further including the step of determining a bending deformation in said test member as $$\Delta\theta = 2\sin^{-1}\left[\frac{(\Delta L_1 - \Delta L_2)}{2S}\right]$$

wherein $\Delta L_1$ and $\Delta L_2$ are respectively said first and second displacements and $S$ is said sensing space.

19. The method of claim 18, further including the step of determining a centerline strain $\epsilon_{cl}$ of said test member that is spaced $S_1$ from said first plane and spaced $S_2$ from said second plane as $$\varepsilon_{cl} = \left(1 + \frac{\Delta L_1 S_2 + \Delta L_2 S_1}{SL_o}\right)\left(\frac{\theta_o + \Delta\theta}{\sin\left(\frac{\theta_o + \Delta\theta}{2}\right)}\right)\left(\frac{\sin\frac{\theta_o}{2}}{\theta_o}\right) - 1$$

wherein $\theta_O$ is an initial bending deformation of said member and Lo is an initial distance between said first and second spatial-position members.

20. The method of claim 19, further including the step of determining a strain $\epsilon_S$ along a surface of said member that is spaced D from said centerline as $$\varepsilon_S = \left(1 + \frac{\Delta L_1(S_2 + D) + \Delta L_2(S_1 - D)}{SL_o}\right)\left(\frac{\theta_o + \Delta\theta}{\sin\left(\frac{\theta_o + \Delta\theta}{2}\right)}\right)\left(\frac{\sin\frac{\theta_o}{2}}{\theta_o}\right) - 1.$$

* * * * *